United States Patent [19]
Martin

[11] Patent Number: 4,661,061
[45] Date of Patent: Apr. 28, 1987

[54] FOUR SIDED ROOT CANAL RASP FOR ROOT CANAL PREPARATION

[76] Inventor: Howard Martin, 909 Pershing Dr., Silver Spring, Md. 20910

[21] Appl. No.: 757,433

[22] Filed: Jul. 22, 1985

[51] Int. Cl.$^4$ .............................................. A61C 0/02
[52] U.S. Cl. ................................................... 433/102
[58] Field of Search ......................................... 433/102

[56] References Cited

U.S. PATENT DOCUMENTS

| | | | |
|---|---|---|---|
| 1,307,446 | 6/1919 | Kerr | 433/102 |
| 2,715,772 | 8/1955 | Fritz | 433/102 |
| 4,231,738 | 11/1980 | Riitano | 433/102 |

FOREIGN PATENT DOCUMENTS 648688 12/1935 Fed. Rep. of Germany ...... 433/102

*Primary Examiner*—Robert Peshock
*Attorney, Agent, or Firm*—Walter G. Finch

[57] ABSTRACT

The invention concerns a dental instrument for performing root canal work. An end portion, integrally connected to the instrument shaft, is provided with four faces of like size, shape and orientation. The four faces are joined to one another by curved, continuous edges. Thus, the end portion has a square cross-section, provided so canal walls can be rasped at four points while leaving the walls of the canal smooth. Because the face edges meet at one point, a separate tip element is not necessary.

14 Claims, 5 Drawing Figures

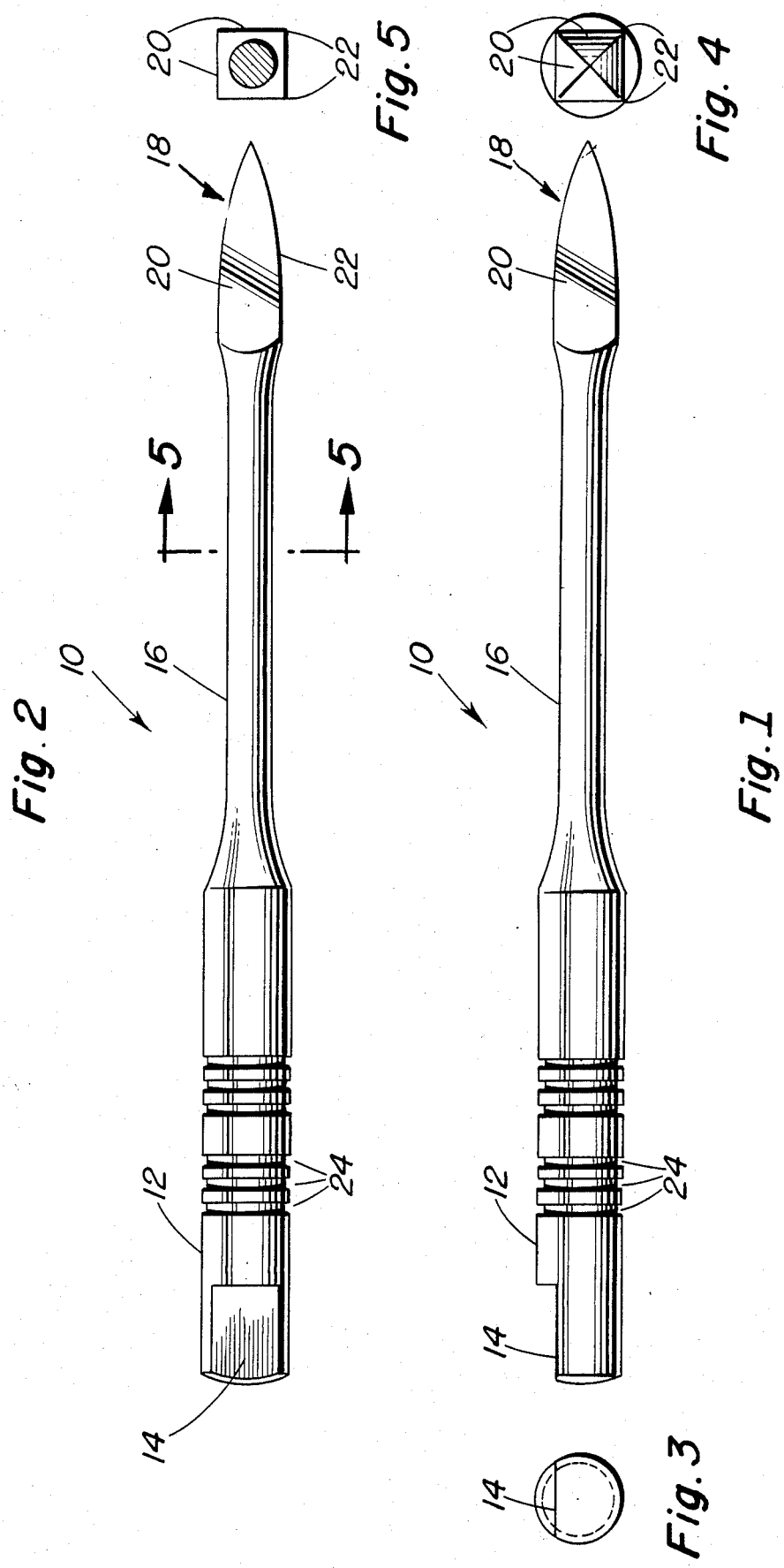

FOUR SIDED ROOT CANAL RASP FOR ROOT CANAL PREPARATION

BACKGROUND OF THE INVENTION

The invention relates to a dental tool for root canal preparation.

Recent endodontic studies have discussed various methods of root canal preparation. The authors of some of these studies have raised questions about the effectiveness of hand instruments and have preferred the ease of use and efficiency of time of rotary instruments. The elimination of morphologic aberrations from the canal is important for debris removal and also to effect smoothness of the intracanal walls for ease of filling. However, no matter what rotary instrument is used, some hand instrumentation must be done, but the bulk of the canal preparation can be accomplished by a properly designed rotary instrument. In this manner the labor involved, in using the final hand instrument at the curved tip (apex) of the root canal, is reduced. Clinical studies have shown the importance of flaring the canal for debridement and instrumentation, and to allow the placement of more irrigating solution into the canal for disinfection and cleansing. Today many dentists use a combination of rotary instruments to widen or flare the orifice, cervical, and middle portions of the canal, allowing the apical portion to be easily accessed for final hand instrumentation.

The prior art instrument commonly used for this purpose is the Gates-Glidden drill. This drill has a short flame-shaped, pear-shaped, head with side cutting blades spiraling slightly with a wide rake angle. A Gates-Glidden drill usually has a short non-cutting guide at the tip to minimize its potential for perforating the root surface of the canal, but can also be obtained without the non-cutting guide. The flame-shaped head is connected to the shank by a long thin neck. The tip has been known to break during use, thus preventing further root canal treatment. Unintentional perforations are also common with drills of the Gates-Glidden type, the #1 drill being equal to a #40 hand file instrument which is larger than typical root canals. The #40 hand instrument is used only after much preparation, and usually in straight canals. Instruments normally used in root canal work include a hand instrument of #15 which has a 0.15 mm tip. Others so used include #20, #25, #30 etc., being 0.05 mm larger, incrementally. Therefore, it is apparent the #1 Gates drill (0.40 mm) is too large for root canal work. The #2 Gates drill is the size of a #60 (0.60 mm tip) hand instrument, while the #3, 4, 5 and 6 Gates drills are 0.80, 1.0, 1.2, and 1.4 mm, respectively. Most rotary instruments have a tendency to transport at least part of the root canal, particularly in curved canals. Often a portion of the root canal has not been touched by the drill, leaving residual tissue, which may result in further contamination. The Gates drill will straighten canals and leave only an apical curve. Due to its pear shape, the Gates drill will notch and furrow the internal wall of the canal, leaving it grooved and forming a repository for debris. As a result, more hand instrumentation is necessary. Due to the pear shape, debris is forced ahead of the drill, instead of being withdrawn by the drill, allowing dentin particles to remain in the canal, requiring further hand instrumentation and irrigation.

SUMMARY OF THE INVENTION

The invention involves a drill instrument to be attached to an engine rotary handpiece, for use in root canal preparation having a long thin shaft with a weak spot which facilitates breakage, should the instrument become wedged in a canal. The end portion of the instrument is provided with four faces of like size, shape and orientation for rasping canal walls at four points, while leaving the canal walls smooth. With this four-sided design, debris is forced out of the canal, away from the instrument end, thus avoiding clogging of the canal. The point of the instrument end portion is a continuation of four curved edges which join the four faces, and as such, is formed as part of the end portion. The four-sided, and, thus, square cross-section, also allows proper funneling into the root canal orifice and provides better tactile sense of the canal. The present invention also eliminates the possibility of over-cutting the canal in a particular area, which in turn reduces the possibility of perforation, weakening the root structure, or stripping away dentin in a particular area of the canal.

BRIEF DESCRIPTION OF THE DRAWINGS

FIG. 1 shows a side view of the present invention.

FIG. 2 shows a top view of the present invention.

FIG. 3 shows a back view of the present invention as viewed in FIG. 1.

FIG. 4 is a front view of the instrument as shown in FIG. 1.

FIG. 5 is a cross-section of the instrument as shown in FIG. 2.

DETAILED DESCRIPTION OF THE INVENTION

FIG. 1 shows a root canal dental instrument, generally at 10, in accordance with the present invention. As viewed in FIG. 1, the dental instrument 10 has a shank portion 12 which includes a flat surface 14. The flat surface 14 facilitates connection of the dental instrument to a rotary handpiece, for instance. Integrally connected to the shank portion 12 is a shaft portion 16 which is of length appropriate for manipulation by a dentist. The shaft portion 16 has a diameter which is small enough to provide a weak spot, to facilitate breakage of the instrument 10 should it become lodged in a canal. In prior art hand dental instruments, such a weak spot has not been included. Thus, when the prior art instruments become wedged, the very tip breaks off, which, being small (0.15 mm or less), is difficult to remove. End portion 18 is approximately 0.15 mm in diameter, and is integrally connected to the shaft portion 16, portions 12, 16 and 18 forming the body of the instrument. In accordance with the present invention, the end portion 18 may vary in size in increments of 0.05 mm and includes a plurality of faces, typically of the same size, shape and orientation. A corresponding plurality of edges 22 join the faces 20 to one another. As is evident, the edges 22 each form a continuous curve from the wider section of the end portion 18 to a point. Grooves 24 in the shank portion 12 are provided to enhance handling of the dental instrument 10.

In the preferred embodiment, four faces 20 are used, such that end portion 18 has a square cross-section. With a four-faced hand instrument, a canal can be rasped at four points, while leaving the canal walls smooth. Additionally, debris are carried or funneled out of the canal by the instrument, which avoids clogging of the canal. Proper tactile sense is also realized by the four-sided instrument.

FIG. 2 shows a top view of the dental instrument portrayed in FIG. 1. Here, it is evident that the dental instrument 10 is symmetric about the instrument's longitudinal axis, except for flat surface 14. The flat surface 14 is located only on the upper side of the dental instrument 10.

FIG. 3 is an end view of the dental instrument 10, wherein the details of the flat surface 14 are more readily apparent. The flat surface 14, a connection means, is slipped into a handle or other appropriate device for easy manipulation thereof.

A front view of the instrument 10 is shown in FIG. 4. Here, the symmetrical nature of the dental instrument 10 is again apparent. The four faces 20 of the end portion 18 are joined via curved edges 22 which converge in continuous lines to a point.

FIG. 5 reveals a section view of the dental instrument 10, taken at line 5—5 of FIG. 2. The square cross-section, owing to the equal size, shape and like orientation of faces 20, is apparent. It is readily seen that the width of the end portion 18 (at its largest section) is greater than the radius of the shaft 16.

Other modifications are apparent to those skilled in the art which are in keeping with the spirit of the present invention, the scope of which being defined by the appended claims.

What is claimed is:

1. A rotary dental root canal instrument having:
   a shank portion;
   a long thin shaft portion integrally connected to the shank portion; and
   an end portion integrally connected to the shaft portion opposite the shank portion; the end portion having a plurality of faces which join one another along a plurality of edges, said plurality of faces being of equal size, shape and orientation, with said edges meeting at a point, and with said edges being curved in an unbroken line toward each other whereby when the canal is being rasped the debris is forced out of the canal away from the instrument end.

2. A dental instrument as recited in claim 1, wherein the plurality of faces comprise four faces.

3. A dental instrument as recited in claim 2, wherein the plurality of edges comprise four edges.

4. A dental instrument as recited in claim 3, wherein a cross-section taken at the end portion is square.

5. A dental instrument as recited in claim 1, and means for connecting said shank portion to said end portion.

6. A dental instrument as recited in claim 1, wherein the end portion has four faces of like size, shape, and orientation.

7. A dental instrument as recited in claim 6, wherein the four faces joined to one another by four edges.

8. A dental instrument as recited in claim 7, wherein the edges meet at a point.

9. A dental instrument as recited in claim 8, wherein the edges are curved in an unbroken line toward each other.

10. A dental instrument as recited in claim 9, and means for connecting said shank portion to said shaft portion.

11. A dental instrument as recited in claim 10, wherein the end portion is at least 0.15 mm in diameter.

12. A dental instrument as recited in claim 5, wherein the end portion is at least 0.15 mm in diameter.

13. A dental instrument as recited in claim 11, wherein the end portion is at least one 0.05 mm increment greater in diameter than 0.15 mm.

14. A dental instrument as recited in claim 12, wherein the end portion is at least one 0.05 mm increment greater in diameter than 0.15 mm.

* * * * *